US011090121B2

(12) United States Patent
Culala

(10) Patent No.: US 11,090,121 B2
(45) Date of Patent: Aug. 17, 2021

(54) LUNG ANALYSIS AND REPORTING SYSTEM

(71) Applicant: GYRUS ACMI, INC., Southborough, MA (US)

(72) Inventor: Nathaniel C. Culala, Bothell, WA (US)

(73) Assignee: GYRUS ACMI, INC., Westborough, MA (US)

( * ) Notice: Subject to any disclaimer, the term of this patent is extended or adjusted under 35 U.S.C. 154(b) by 53 days.

(21) Appl. No.: 16/288,642

(22) Filed: Feb. 28, 2019

(65) Prior Publication Data

US 2020/0222120 A1    Jul. 16, 2020

Related U.S. Application Data

(60) Provisional application No. 62/792,706, filed on Jan. 15, 2019.

(51) Int. Cl.
| | |
|---|---|
| *A61B 34/10* | (2016.01) |
| *A61B 1/267* | (2006.01) |
| *G06T 19/00* | (2011.01) |
| *A61B 6/03* | (2006.01) |
| *G06T 7/00* | (2017.01) |

(Continued)

(52) U.S. Cl.
CPC ............ *A61B 34/10* (2016.02); *A61B 1/2676* (2013.01); *A61B 6/032* (2013.01); *G06T 7/0012* (2013.01); *G06T 19/003* (2013.01); *A61B 2017/00809* (2013.01); *A61B 2034/105* (2016.02); *A61B 2034/107* (2016.02); *G06T 7/11* (2017.01); *G06T 2207/10081* (2013.01); *G06T 2207/30061* (2013.01); *G06T 2210/41* (2013.01); *G06T 2219/028* (2013.01)

(58) Field of Classification Search
CPC ....... G06T 7/0012; G06T 7/0014; G06T 7/11; G06T 7/90; G06T 19/003; G06T 2207/10024; G06T 2207/10081; G06T 2207/30061; G06T 2210/41; G06T 2219/028; A61B 1/2676; A61B 6/032; A61B 6/50; A61B 6/5217; A61B 2017/00809; A61B 34/10; A61B 2034/105; A61B 2034/107; A61B 2576/02
See application file for complete search history.

(56) References Cited

U.S. PATENT DOCUMENTS

| | | | | |
|---|---|---|---|---|
| 2014/0275952 | A1* | 9/2014 | Monroe | G06T 19/00 600/407 |
| 2015/0238270 | A1* | 8/2015 | Raffy | A61B 5/7275 600/407 |

(Continued)

OTHER PUBLICATIONS

Revel et al. "Automated lobar quantification of emphysema in patients with severe COPD." European radiology 18.12 (2008): 2723-2730. (Year: 2008).*

*Primary Examiner* — Katrina R Fujita
(74) *Attorney, Agent, or Firm* — Clements Bernard Walker; Michael S. Smith

(57) ABSTRACT

A system and method for analyzing scan data of a lung and presenting a lung candidacy report. The lung candidacy report includes determinations represented visually of whether lung lobes are suitable candidates for a bronchoscopy guided lung volume reduction procedure. The lung candidacy report includes emphysema values and fissure integrity determined from the scan data.

6 Claims, 3 Drawing Sheets

(51) Int. Cl.
*A61B 17/00* (2006.01)
*G06T 7/11* (2017.01)

(56) References Cited

U.S. PATENT DOCUMENTS

2016/0328850 A1* 11/2016 Yin .................. G16H 30/40
2017/0224301 A1* 8/2017 Radhakrishnan ...... A61B 6/563

* cited by examiner

LUNG ANALYSIS AND REPORTING SYSTEM

BACKGROUND

Analysis of the patient's high-resolution computed tomography (HRCT) information and quantitative computed tomography (QCT) results are critical to successful patient outcomes. Reliable key measures of emphysema severity, fissure integrity, and heterogeneity are needed to allow physicians to quickly and confidently identify a target lobe and potential candidates for treatment in order to ensure a successful bronchoscopy guided lung volume reduction (BLVR) procedure.

SUMMARY

The present disclosure provides improved systems and methods for providing lung candidacy information to health care professionals.

The present disclosure provides an exemplary system having a processing device that receives three-dimensional image data of at least a portion of a lung of a person, the three-dimensional image data includes volumetric data (i.e., voxels). The processing device delineates lung lobes and lung fissures from the voxels and for each of the voxels in a delineated lung lobe, generates emphysema scores for each of the lung lobes based on a predefined threshold of radio density values or a threshold range of radio density values. The processing device generates fissure integrity scores for each of the lung fissures based on the voxels, generates heterogeneity scores for at least two lobes based on the emphysema score of a target lobe and the emphysema score of a lobe adjacent to the target lobe, and generates a report that includes the emphysema scores, fissure integrity score and heterogeneity scores. The system includes an output device that is in signal communication with the processing device. The output device outputs the report.

In one aspect of the disclosure, the report includes a visual representation of an emphysema level based on the generated emphysema scores, a visual representation of fissure integrity based on the generated fissure integrity scores, and a visual representation of lung lobe candidacy. The visual representation of the emphysema level includes a visual representation of each of the lung lobes, wherein the emphysema level is visually represented by a least one of a particular color or pattern of a corresponding lung lobe visual representation. The visual representation of the fissure integrity includes a visual representation of each of the delineated fissures, wherein the delineated fissures are visually represented by a least one of a particular color or pattern based on the fissure integrity score.

In another aspect of the disclosure, the visual representation of the lung lobe candidacy includes a lung lobe candidacy icon, the lung lobe candidacy icon is visually associated with a corresponding lung lobe visual representation. The lung lobe candidacy icon includes the emphysema score and the heterogeneity score of the associated lung lobe and the fissure integrity score of the fissure adjacent to the associated lung lobe. The lung lobe candidacy icon includes a visual indication of meeting a predefined inclusion criterion. The visual indication of meeting the predefined inclusion criteria includes representing at least a portion of the lung lobe candidacy icon in at least one of a unique color or pattern.

Further features, advantages, and areas of applicability will become apparent from the description provided herein.

It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely illustrative in nature and is not intended to limit the present disclosure, application, or uses. The following description explains, by way of illustration only and not of limitation, various embodiments of devices and methods for analyzing and providing a comprehensive report for use in determining candidacy of lung lobes for a pending bronchoscopy guided lung volume reduction (BLVR) procedure.

An embodiment describes a process to automate, display, interact with and characterize aspects of the lung. When the human lung is imaged in vivo with an imaging acquisition device, that image can be reconstructed and evaluated to depict normal and diseased states. Because of the various subclasses of disease and the various depictions (phenotypes) of a disease entity, evaluation of lobular regions of the lung and the fissures separating them are important to accurately characterize disease and predict response to BLVR therapy.

This disclosure includes systems and methods to provide visualization of lung lobes, completeness of fissures and values related to the extent of emphysema in an automated way to enable clinical decision making.

The left and right lungs are each divided into a plurality of lobes by deep clefts, which are the interlobar fissures, referred to herein simply as fissures. The outer surface of the lungs is lined by pleura, including an inner layer which is the visceral pleura which dips into the fissures to surround the lobes. The fissures therefore are the joints between the lobes of the lung and are defined by the outermost surface of the lobes and the visceral pleura at the locations where the lobes abut each other. Therefore, although the fissure itself is actually an interface between abutting lobes, it is the very thin layer of the lobar interfaces that can be detected on a volumetric image and is interpreted as being the fissure. The right lung includes three lobes (the upper, middle, and lower lobes) which are divided by two fissures, known as the oblique and the horizontal fissures. The left lung includes two lobes (the upper and lower lobes) with one fissure, the oblique fissure, between them.

The edges of the lobes and the pleura that lines the lobes define the fissures and separate the lobes such that the ventilation of each lobe separates from that of adjacent abutting lobes. In addition, the pleura normally form a smooth surface, allowing abutting lobes to slide relative to each other during inhalation and exhalation. However, in certain disease conditions, the pleura may become thickened or adherent. In addition, abutting lobes may adhere to each other and the pleura and lung margins that normally define the fissure may be lost. The fissure is described by a level of completeness and below a certain level air can flow between the lobes. Various embodiments described herein identify the fissure completeness using volumetric radiological images and present them visually in a 2D image.

Figure 1:
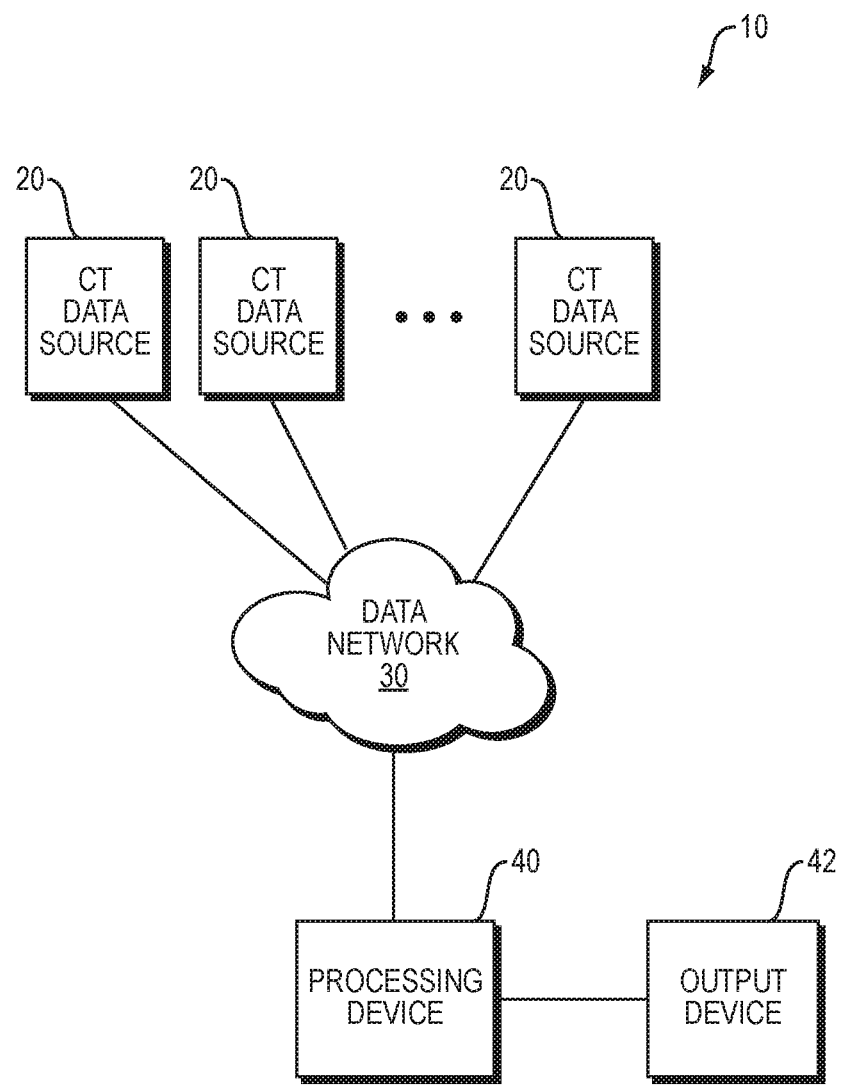
FIG. 1 is a block diagram of an exemplary system formed in accordance with an embodiment of the present invention.

FIG. 1 shows an exemplary lung visualization system 10, which may include a processor, such as a processor 40 in a computer, and may also include an output device 42, such as a visual display (monitor or screen) or a printing device. The system 10 may also include instructions included in software (computer readable media), stored in memory of the system, and operable on the processor 40. The software may include instructions for the processor 40 to perform the various steps and methods described herein, including instructions to receive patient data including volumetric imaging data from data sources 20 possibly connected to the processor 40 via a public and/or private data network 30, analyze the data to characterize the lung, and generate images resulting from the analysis of the imaging data. The generated images may be transmitted to a customer computing device via the data network 30 or may be outputted in a physical form and delivered to the customer.

Examples of the embodiments may be implemented using a combination of hardware, firmware, and/or software. For example, in many cases some or all of the functionality provided by examples may be implemented in executable software instructions capable of being carried on a programmable computer processor. Likewise, some examples of the invention include a computer-readable storage device on which such executable software instructions are stored. In certain examples, the system processor itself may contain instructions to perform one or more tasks. System processing capabilities are not limited to any specific configuration and those skilled in the art will appreciate that the teachings provided herein may be implemented in a number of different manners.

Figure 2:
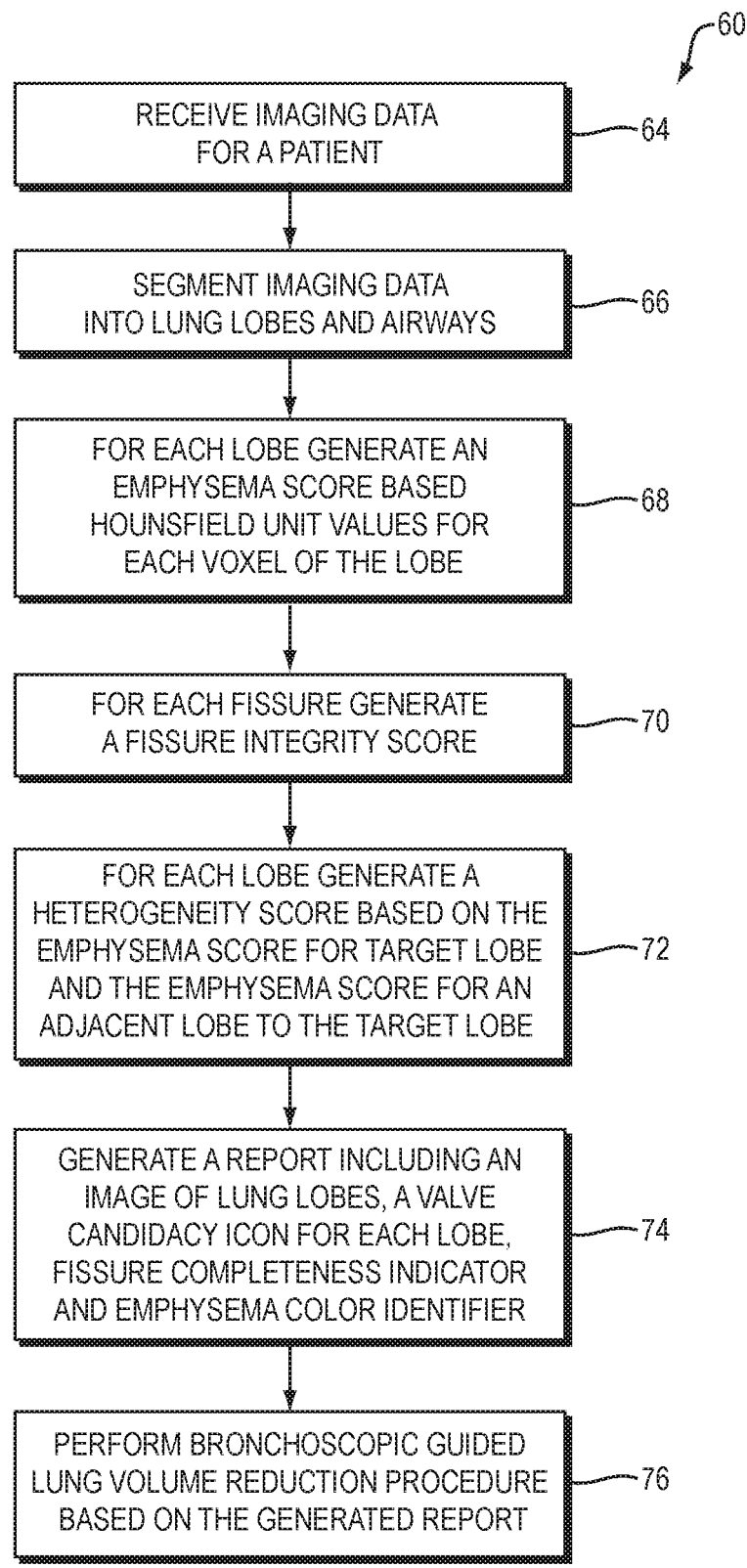
FIG. 2 is a flow diagram of an exemplary process performed by at least the system of FIG. 1.

FIG. 2 shows a flowchart of a lung characterization and visualization method 60 which may be carried out using software as part of the system 10, for example. At step 64, volumetric radiological images or imaging data of a patient are transmitted to the processing device 40 from the data sources 20. The volumetric radiological images or imaging data may be computed tomography (CT) scans, magnetic resonance imaging (MRI) scans, and/or position emission tomography (PET) scans, from which a series of two-dimensional planar images (referred to herein as two-dimensional volumetric images or two-dimensional images) can be produced in multiple planes.

At step 66, the lungs, airways, and/or blood vessels are segmented using the received image data. The methods of performing lung, airway and vessel segmentation from the volumetric images or imaging data may be those described in various research papers (e.g., Strange C; Herth, F J; Kovitz, K L; McLennan, G; Ernst, A; Goldin J; et al; Design of the Endobronchial Valve for Emphysema Palliation Trial (VENT): a nonsurgical method of lung volume reduction, BMC Pulm Med. 2007 Jul. 3; 7:10.) Segmentation of the lungs, airways, and vessels results in identification of the lung tissue, airways, and vessels as distinct from the surrounding tissues and of separation of the lungs, airways, and vessels into smaller distinct portions which may be individually identified in accordance with standard pulmonary anatomy. Lung lobes are then delineated from separated data.

At step 68, for each lobe an emphysema score is generated based on Hounsfield unit (i.e., radiodensity (HU)) values for each voxel in the lung lobe data of the targeted lobe. In one embodiment, the emphysema score is identified as a percentage of emphysema in the lobe. The percentage is calculated by determining what percentage of lobe voxels have a Hounsfield unit value less than a threshold amount (e.g. −920 HU) or within a range of Hounsfield unit values.

Next, at step 70, a fissure completeness value is generated for each of three fissures based an analysis of on the imaging data. An exemplary method for calculating the fissure completeness value is described in Brown, M S; Ochs, R; Abtin, F; Ordookhani, A; Brown, M; Kim, H; Shaw, G; Chong, D; Goldin, J. Automated Quantitative Assessment of Lung Fissure Integrity on CT. Proceedings of the First International Workshop on Pulmonary Image Analysis; New York, USA, 2008: 93-102.

Then, at step 72, a heterogeneity score is generated for each lobe based on the difference between the emphysema score for the target lobe and the emphysema score for a lobe adjacent to the target lobe.

Next, at step 74, a report is generated that includes an image that includes BLVR candidacy icons for at least two lobes, fissure completeness indicators and emphysema level visual identifier.

Then, at step 76, a health care provider performs a BLVR procedure, i.e. places one or more interbronchial valves (IBVs) in a lung lobe, based on a review of the generated report. An exemplary IBV is the IBV valve system produced by Olympus®.

Figure 3:
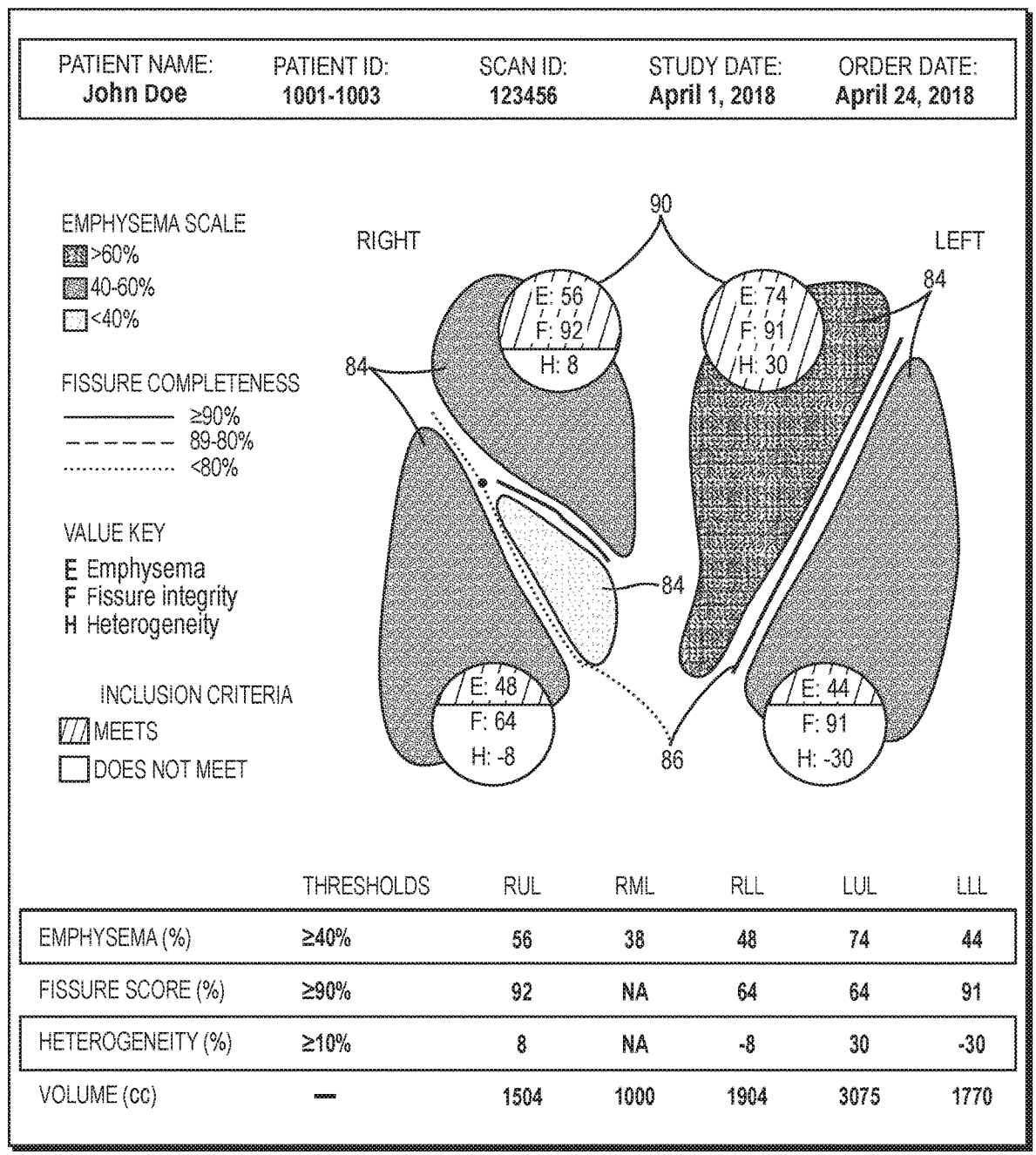
FIG. 3 is an image of a report generated by the system of FIG. 1 in accordance with the process shown in FIG. 2.

FIG. 3 illustrates an exemplary report 80 generated by the processing device 40 (step 74 of FIG. 2). The report 80 may be generated in any of a number of different formats and delivered any number of different ways to the entity (e.g., health care professional responsible for treating the patient associated with the analyzed image data) who initially made a request for the report. The report 80 includes a lung display area 82 that includes an image of lung lobes 84. The previously calculated emphysema score is represented graphically on the image of the lobes 84 either by a particular pattern or color based on where the emphysema score falls within a predefined scale—see emphysema score scale to the left of the lung display area 82.

Fissure lines 86 are shown between their respective lobes in the lung display area 82. The fissure lines 86 are presented by a particular line pattern and/or color based on the previously calculated fissure completeness score and a fissure completeness scale—see fissure completeness scale shown below the emphysema score scale.

BLVR candidacy icons 90 are shown next to or overlapping the associated lung lobe in the lung display area 82. In this example, the icons 90 are only shown for the right upper lobe, right lower lobe, left upper lobe, and left lower lobe. However, the calculated scores are shown for all lobes in a table at bottom of the report 80. The BLVR candidacy icons 90 include the calculated scores for emphysema, fissure completeness and heterogeneity. The background color or pattern for each score in the icons 90 represent meeting or not meeting a predefined inclusion criteria (i.e., threshold) for each of the scores. The icons 90 provide a visual tool for allowing a health care professional to determine what lobes are good candidates for a BLVR procedure. In the example of FIG. 3, the left upper lobe is the only lobe where all three scores meet the associated predefined criteria (i.e., thresholds). The criteria was determined based on experience gained from multiple clinical trials.

The description of the invention is merely exemplary in nature and variations that do not depart from the gist of the invention are intended to be within the scope of the invention. Such variations are not to be regarded as a departure from the spirit and scope of the invention.

Embodiments

A. A method comprising: receiving three-dimensional image data of at least a portion of a lung of a person, the three-dimensional image data comprises voxels; delineating lung lobes and lung fissures from the voxels; for each of the voxels in a delineated lung lobe, generating emphysema scores for each of the lung lobes based on a predefined threshold of radio density values or a threshold range of radio density values; generating fissure integrity scores for each of the lung fissures based on the voxels; generating heterogeneity scores for at least two lobes based on the emphysema score of a target lobe and the emphysema score of a lobe adjacent to the target lobe; generating a report comprising the emphysema scores, fissure integrity score and heterogeneity scores; and outputting the report.

B. The method of A, wherein the report comprises: a visual representation of an emphysema level based on the generated emphysema scores; a visual representation of fissure integrity based on the generated fissure integrity scores; and a visual representation of lung lobe candidacy.

C. The method of B, wherein the visual representation of the emphysema level comprises a visual representation of each of the lung lobes, wherein the emphysema level is visually represented by a least one of a particular color or pattern of a corresponding lung lobe visual representation.

D. The method of B or C, wherein the visual representation of the fissure integrity comprises a visual representation of each of the delineated fissures, wherein the delineated fissures are visually represented by a least one of a particular color or pattern based on the fissure integrity score.

E. The method of any of B-D, wherein the visual representation of the lung lobe candidacy comprises a lung lobe candidacy icon, the lung lobe candidacy icon is visually associated with a corresponding lung lobe visual representation.

F. The method of E, wherein the lung lobe candidacy icon comprises the emphysema score and the heterogeneity score of the associated lung lobe and the fissure integrity score of the fissure adjacent to the associated lung lobe.

G. The method of E or F, wherein the lung lobe candidacy icon comprises a visual indication of meeting a predefined inclusion criterion.

H. The method of G, wherein the visual indication of meeting the predefined inclusion criteria comprises representing at least a portion of the lung lobe candidacy icon in at least one of a unique color or pattern.

I. The method of any of A-H, wherein the radio density values are represented in Hounsfield unit values.

J. A system comprising: a processing device configured to: receive three-dimensional image data of at least a portion of a lung of a person, the three-dimensional image data comprises voxels; delineate lung lobes and lung fissures from the voxels; for each of the voxels in a delineated lung lobe, generate emphysema scores for each of the lung lobes based on a predefined threshold of radio density values or a threshold range of radio density values; generate fissure integrity scores for each of the lung fissures based on the voxels; generate heterogeneity scores for at least two lobes based on the emphysema score of a target lobe and the emphysema score of a lobe adjacent to the target lobe; and generate a report comprising the emphysema scores, fissure integrity score and heterogeneity scores; and an output device in signal communication with the processing device, the output device configured to output the report.

K. The system J, wherein the report comprises: a visual representation of an emphysema level based on the generated emphysema scores; a visual representation of fissure integrity based on the generated fissure integrity scores; and a visual representation of lung lob candidacy.

L. The system of K, wherein the visual representation of the emphysema level comprises a visual representation of each of the lung lobes, wherein the emphysema level is visually represented by a least one of a particular color or pattern of a corresponding lung lobe visual representation.

M. The system of K or L, wherein the visual representation of the fissure integrity comprises a visual representation of each of the delineated fissures, wherein the delineated fissures are visually represented by a least one of a particular color or pattern based on the fissure integrity score.

N. The system of any of K-M, wherein the visual representation of the lung lobe candidacy comprises a lung lobe candidacy icon, the lung lobe candidacy icon is visually associated with a corresponding one of the lung lobe visual representations.

O. The system of N, wherein the lung lobe candidacy icon comprises the emphysema score and the heterogeneity score of the associated lung lobe and the fissure integrity score of the fissure adjacent to the associated lung lobe.

P. The system of N or O, wherein the lung lobe candidacy icon comprises a visual indication of meeting a predefined inclusion criterion.

Q. The system of P, wherein visual indication of meeting the predefined inclusion criteria comprises representing at least a portion of the lung lobe candidacy icon in at least one of a unique color or pattern.

R. The system of any of J-Q, wherein the radio density values are represented in Hounsfield unit values.

S. A non-transitory computer-readable recording medium with an executable program stored thereon, the program causing a processor to: receive three-dimensional image data of at least a portion of a lung of a person, the three-dimensional image data comprises voxels; delineate lung lobes and lung fissures from the voxels; for each of the voxels in a delineated lung lobe, generating emphysema scores for each of the lung lobes based on a predefined threshold of radio density values or a threshold range of radio density values; generate fissure integrity scores for each of the lung fissures based on the voxels; generate heterogeneity scores for at least two lobes based on the emphysema score of a target lobe and the emphysema score of a lobe adjacent to the target lobe; generate a report comprising the emphysema scores, fissure integrity score and heterogeneity scores; and output the report to an output device.

T. The non-transitory computer-readable recording medium of claim 19, wherein the report comprises: a visual representation of an emphysema level based on the generated emphysema scores; a visual representation of fissure integrity based on the generated fissure integrity scores; and a visual representation of lung lobe candidacy.

U. A system comprising: a processing device configured to: receive emphysema scores for each lung lobe previously delineated from three-dimensional image data of at least a portion of a lung of a person; receive fissure integrity scores for each of the lung fissures previously delineated from the three-dimensional image data; receive heterogeneity scores for at least two lobes; and generate a report comprising the emphysema scores, fissure integrity score and heterogeneity scores; and an output device in signal communication with the processing device, the output device configured to output the report.

V. The system U, wherein the report comprises: a visual representation of an emphysema level based on the generated emphysema scores; a visual representation of fissure integrity based on the generated fissure integrity scores; and a visual representation of lung lobe candidacy.

W. The system of V, wherein the visual representation of the emphysema level comprises a visual representation of each of the lung lobes, wherein the emphysema level is visually represented by a least one of a particular color or pattern of a corresponding lung lobe visual representation.

X. The system of V or W, wherein the visual representation of the fissure integrity comprises a visual representation of each of the delineated fissures, wherein the delineated fissures are visually represented by a least one of a particular color or pattern based on the fissure integrity score.

Y. The system of any of V-X, wherein the visual representation of the lung lobe candidacy comprises a lung lobe candidacy icon, the lung lobe candidacy icon is visually associated with a corresponding one of the lung lobe visual representations.

Z. The system of Y, wherein the lung lobe candidacy icon comprises the emphysema score and the heterogeneity score of the associated lung lobe and the fissure integrity score of the fissure adjacent to the associated lung lobe.

AA. The system of Y or Z, wherein the lung lobe candidacy icon comprises a visual indication of meeting a predefined inclusion criterion.

AB. The system of AA, wherein visual indication of meeting the predefined inclusion criteria comprises representing at least a portion of the lung lobe candidacy icon in at least one of a unique color or pattern.

AC. The system of any of U-AB, wherein the radio density values are represented in Hounsfield unit values.

Although the preferable embodiments of the present invention have been described hitherto, the present invention is not limited to these embodiments. Additions, omissions, substitutions, and other modifications can be made without departing from the spirit or scope of the present invention.

What is claimed is:

1. A method comprising:
   receiving three-dimensional image data of at least a portion of a lung of a person, the three-dimensional image data comprises voxels;
   delineating lung lobes and lung fissures from the voxels;
   for each of the voxels in a delineated lung lobe, generating emphysema scores for each of the lung lobes based on a predefined threshold of radio density values or a threshold range of radio density values;
   generating fissure integrity scores for each of the lung fissures based on the voxels;
   generating heterogeneity scores for at least two lobes based on the emphysema score of a target lobe and the emphysema score of a lobe adjacent to the target lobe;
   generating a report comprising the emphysema scores, fissure integrity scores and heterogeneity scores; and
   outputting the report, wherein the report comprises:
      a visual representation of an emphysema level based on the generated emphysema scores, the visual representation of the emphysema level comprising a visual representation of each of the lung lobes, the emphysema level is visually represented by a least one of a particular color or pattern of a corresponding lung lobe visual representation;
      a visual representation of fissure integrity based on the generated fissure integrity scores, the visual representation of the fissure integrity comprising a visual representation of each of the delineated fissures, wherein the delineated fissures are visually represented by a least one of a particular color or pattern based on the fissure integrity score; and
      a plurality of lung lobe candidacy icons, each of the lung lobe candidacy icons is visually associated with a corresponding one of the lung lobe visual representations, the lung lobe candidacy icons comprise a visual indication of meeting a predefined inclusion criterion for each of the scores, the visual indication of meeting the predefined inclusion criteria comprises representing at least a portion of the lung lobe candidacy icon in at least one of a unique color or pattern,
      wherein the lung lobe candidacy icons comprise the emphysema score and the heterogeneity score of the associated lung lobe and the fissure integrity score of the fissure adjacent to the associated lung lobe.

2. The method of claim 1, wherein the radio density values are represented in Hounsfield unit values.

3. The method of claim 1, further comprising performing a bronchoscopic lung volume reduction procedure on the person based on the outputted report.

4. A system comprising:
   a processing device configured to:
      receive three-dimensional image data of at least a portion of a lung of a person, the three-dimensional image data comprises voxels;
      delineate lung lobes and lung fissures from the voxels;
      for each of the voxels in a delineated lung lobe, generates emphysema scores for each of the lung lobes based on a predefined threshold of radio density values or a threshold range of radio density values;
      generate fissure integrity scores for each of the lung fissures based on the voxels;
      generate heterogeneity scores for at least two lobes based on the emphysema score of a target lobe and the emphysema score of a lobe adjacent to the target lobe; and
      generate a report comprising the emphysema scores, fissure integrity score and heterogeneity scores; and
   an output device in signal communication with the processing device, the output device configured to output the report, wherein the report comprises:
      a visual representation of an emphysema level based on the generated emphysema scores, the visual representation of the emphysema level comprising a visual representation of each of the lung lobes, wherein the emphysema level is visually represented by a least one of a particular color or pattern of a corresponding lung lobe visual representation;
      a visual representation of fissure integrity based on the generated fissure integrity scores, the visual representation of the fissure integrity comprising a visual representation of each of the delineated fissures, wherein the delineated fissures are visually represented by a least one of a particular color or pattern based on the fissure integrity score; and
      a plurality of lung lobe candidacy icons, each of the lung lobe candidacy icons is visually associated with a corresponding lung lobe visual representation, the lung lobe candidacy icons comprise a visual indication of meeting a predefined inclusion criterion for each of the scores, the visual indication of meeting the predefined inclusion criteria comprises representing at least a portion of the lung lobe candidacy icon in at least one of a unique color or pattern,
wherein the lung lobe candidacy icons comprise the emphysema score and the heterogeneity score of the associated lung lobe and the fissure integrity score of the fissure adjacent to the associated lung lobe.

5. The system of claim 4, wherein the radio density values are represented in Hounsfield unit values.

6. A non-transitory computer-readable recording medium with an executable program stored thereon, the program causing a processor to:
  receive three-dimensional image data of at least a portion of a lung of a person, the three-dimensional image data comprises voxels;
  delineate lung lobes and lung fissures from the voxels;
  for each of the voxels in a delineated lung lope, generating emphysema scores for each of the lung lobes based on a predefined threshold of radio density values or a threshold range of radio density values;
  generate fissure integrity scores for each of the lung fissures based on the voxels;
  generate heterogeneity scores for at least two lobes based on the emphysema score of a target lobe and the emphysema score of a lobe adjacent to the target lobe;
  generate a report comprising the emphysema scores, fissure integrity score and heterogeneity scores; and
  output the report to an output device,
  wherein the report comprises:
    a visual representation of an emphysema level based on the generated emphysema scores, the visual representation of the emphysema level comprising a visual representation of each of the lung lobes, the emphysema level is visually represented by a least one of a particular color or pattern of a corresponding lung lobe visual representation;
    a visual representation of fissure integrity based on the generated fissure integrity scores, the visual representation of the fissure integrity comprising a visual representation of each of the delineated fissures, wherein the delineated fissures are visually represented by a least one of a particular color or pattern based on the fissure integrity score; and
    a plurality of lung lobe candidacy icons, each of the lung lobe candidacy icons is visually associated with a corresponding one of the lung lobe visual representations, the lung lobe candidacy icons comprise a visual indication of meeting a predefined inclusion criterion for each of the scores, the visual indication of meeting the predefined inclusion criteria comprises representing at least a portion of the lung lobe candidacy icon in at least one of a unique color or pattern,
  wherein the lung lobe candidacy icons comprise the emphysema score and the heterogeneity score of the associated lung lobe and the fissure integrity score of the fissure adjacent to the associated lung lobe.

* * * * *

UNITED STATES PATENT AND TRADEMARK OFFICE
CERTIFICATE OF CORRECTION

| | | |
|---|---|---|
| PATENT NO. | : 11,090,121 B2 | Page 1 of 1 |
| APPLICATION NO. | : 16/288642 | |
| DATED | : August 17, 2021 | |
| INVENTOR(S) | : Nathaniel C. Culala and J. Gregory Little | |

It is certified that error appears in the above-identified patent and that said Letters Patent is hereby corrected as shown below:

On the Title Page

Item (12) should read:
--Culala et al.--

Item (72) Inventor(s) should read:
--Nathaniel C. Culala, Bothell, WA
J. Gregory Little, Park City, UT--

Signed and Sealed this
Third Day of May, 2022

*Katherine Kelly Vidal*

Katherine Kelly Vidal
*Director of the United States Patent and Trademark Office*